(12) United States Patent
Nakao et al.

(10) Patent No.: US 11,469,010 B2
(45) Date of Patent: Oct. 11, 2022

(54) CONDUCTIVE PASTE, STRETCHABLE CONDUCTOR AND ELECTRONIC COMPONENT USING SAME, AND CLOTHES-TYPE ELECTRONIC DEVICE

(71) Applicant: TOYOBO CO., LTD., Osaka (JP)

(72) Inventors: Yuko Nakao, Shiga (JP); Michihiko Irie, Shiga (JP)

(73) Assignee: TOYOBO CO., LTD., Osaka (JP)

( * ) Notice: Subject to any disclaimer, the term of this patent is extended or adjusted under 35 U.S.C. 154(b) by 212 days.

(21) Appl. No.: 16/639,223

(22) PCT Filed: Aug. 22, 2018

(86) PCT No.: PCT/JP2018/031003
§ 371 (c)(1),
(2) Date: Feb. 14, 2020

(87) PCT Pub. No.: WO2019/039511
PCT Pub. Date: Feb. 28, 2019

(65) Prior Publication Data
US 2020/0258655 A1 Aug. 13, 2020

(30) Foreign Application Priority Data
Aug. 24, 2017 (JP) .............................. JP2017-161250

(51) Int. Cl.
*H01B 1/22* (2006.01)
*C09D 5/24* (2006.01)
*H01B 7/06* (2006.01)

(52) U.S. Cl.
CPC ............... *H01B 7/06* (2013.01); *C09D 5/24* (2013.01); *H01B 1/22* (2013.01)

(58) Field of Classification Search
CPC ... H01B 1/00; H01B 1/20; H01B 1/22; H01B 1/24; C09D 5/24
See application file for complete search history.

(56) References Cited

U.S. PATENT DOCUMENTS 10,546,664 B2 * 1/2020 Yonekura ................. H01B 1/22
10,995,232 B2 * 5/2021 Cao ......................... C09D 11/52
2016/0130471 A1 5/2016 Burrows et al.
2017/0153152 A1 6/2017 Yoshida et al.
2018/0061519 A1 * 3/2018 Abe ......................... C08F 20/14
2020/0123306 A1 * 4/2020 Kawagishi ............. C08G 18/42

FOREIGN PATENT DOCUMENTS

| JP | 2002-260442 | 9/2002 |
|---|---|---|
| JP | 3723565 | 12/2005 |
| JP | 2012-54192 | 3/2012 |
| JP | 2015-70917 | 4/2015 |
| JP | 2016-27137 | 2/2016 |
| JP | 2017-029691 | 2/2017 |
| WO | 2008/133073 | 11/2008 |
| WO | 2012/028686 | 3/2012 |
| WO | 2015/174505 | 11/2015 |

OTHER PUBLICATIONS

English language machine translation of JP 2002260442 (pub Sep. 2002).*
English language machine translation of WO 2008/133073 (pub Nov. 2008).*
International Search Report dated Oct. 9, 2018 in International (PCT) Application No. PCT/JP2018/031003.
Ahn et al., "Stretchable electronics: materials, architectures and integrations", J. Phys. D: Appl. Phys., vol. 45, 2012, 103001, pp. 1-14.
Chun et al., "Highly conductive, printable and stretchable composite films of carbon nanotubes and silver," Nature Nanotechnology, vol. 5, Dec. 2010, pp. 853-857.
Notice of Reasons for Refusal dated Mar. 29, 2022, in corresponding Japanese Patent Application No. 2019-537656, with English translation.

* cited by examiner

*Primary Examiner* — Mark Kopec
(74) *Attorney, Agent, or Firm* — Wenderoth, Lind & Ponack, L.L.P.

(57) ABSTRACT

A stretchable conductor forming paste containing a conductive filler, a polyurethane elastomer having a glass transition temperature (Tg) of −60° C. to −10° C. and a urethane group concentration of 3000 to 4500 m equivalent/kg, and an organic solvent. Preferably, a total amount of components excluding the solvent is 100 parts by mass, a total of the conductive filler is 70 to 95 parts by mass, and an amount of the polyurethane elastomer is 5 to 30 parts by mass. The obtained paste is printed or coated and then dried to obtain a stretchable conductor, capable of forming a wiring line having good repeated stretchability.

8 Claims, No Drawings

CONDUCTIVE PASTE, STRETCHABLE CONDUCTOR AND ELECTRONIC COMPONENT USING SAME, AND CLOTHES-TYPE ELECTRONIC DEVICE

TECHNICAL FIELD

The present invention relates to a conductive paste composed of a conductive filler and a binder resin, and particularly relates to a conductive paste capable of forming an electric conductor having stretchability. The present invention also relates to a stretchable conductor, an electronic component, and a clothes-type electronic device manufactured using the conductive paste.

BACKGROUND ART

In recent years, wearable electronic devices have been developed which are intended to use electronic devices having input/output, calculation, and communication functions in close proximity to or in contact to the body. As wearable electronic devices, devices having accessory-type external shapes such as watches, glasses, and earphones, and textile-integrated clothes-type electronic devices in which electronic functions are incorporated into clothes are known. An example of such a textile-integrated device is disclosed in Patent Document 1.

The electronic devices require an electrical wiring line for power supply and signal transmission. In particular, in textile-integrated wearable electronic devices and devices using stretchable base materials, the electrical wiring line is required to have stretchability in accordance with a stretchable base material. Usually, an electrical wiring line made of a metal wire or a metal foil is not practically stretchable in essentials. Therefore, such a method that the metal wire or metal foil is placed in a corrugated or repeated horseshoe shape to give a pseudo stretching function is used.

In the case of the metal wire, a wiring line can be formed by regarding the metal wire as an embroidery thread and sewing it onto clothes. However, it is obvious that this method is not suitable for mass production.

A method of forming a wiring line by etching a metal foil is a general method for producing a printed wiring board. A technique is known in which a metal foil is bonded to a stretchable resin sheet, and a corrugated wiring line is formed by a technique similar to that of a printed wiring board to make a pseudo stretchable wiring line (see Non-Patent Document 1). Such a technique is to give pseudo stretchability by torsional deformation of the corrugated wiring part. However, when excessive deformation is applied, permanent plastic deformation occurs in the metal foil, and there is also a problem in durability of the wiring line.

As a technique for realizing a stretchable conductor wiring line, a method using a special conductive paste has been proposed. Conductive particles such as silver particles, carbon particles, and carbon nanotubes, and elastomers such as stretchable urethane resin, natural rubber, synthetic rubber, solvent, and the like are kneaded to form a paste, and the wiring line is printed and drawn directly on clothes or in combination with a stretchable film base material (see Non-Patent Document 2).

Macroscopically, a conductive composition composed of conductive particles and a stretchable binder resin can realize a stretchable conductor. Microscopically, the conductive composition obtained from such a paste is partially deformed in the resin binder when subjected to external force and maintains its conductivity within a range in which the electrical chain of the conductive particles is not interrupted. The specific resistance observed macroscopically is higher than that of metal wires and metal foils. However, because the composition itself has stretchability, there is no need to adopt a shape such as a corrugated wiring line, and there is a high degree of freedom in the wiring width and thickness, so that it is practically possible to realize a low resistance wiring line as compared to the metal wires.

Patent Document 1 discloses a technique for suppressing a decrease in conductivity at the time of elongation by combining silver particles and silicone rubber and further covering a conductive film on a silicone rubber substrate with silicone rubber. Patent Document 2 discloses a combination of silver particles and a polyurethane emulsion, and it is said that a conductive film having high conductivity and high elongation rate can be obtained. Further, many examples have been proposed in which characteristics are improved by combining conductive particles having a high aspect ratio such as carbon nanotubes and silver particles.

Further, Patent Document 3 discloses a technique for directly forming an electrical wiring line on clothes using a printing method. However, there is no detailed description of the binder component that greatly affects the repeated durability.

PRIOR ART DOCUMENTS

Patent Documents

Patent Document 1: JP 2015-70917 A
Patent Document 2: JP 2012-54192 A
Patent Document 3: JP 3723565 B2

NON PATENT DOCUMENTS

Non Patent Document 1: Jong-Hyun Ahn and Jung Ho Je, "Stretchable electronics: materials, architectures and integrations" J. Phys. D: Appl. Phys. 45 (2012) 103001

Non Patent Document 2: Kyoung-Yong Chun, Youngseok Oh, Jonghyun Rho, Jong-Hyun Ahn, Young-Jin Kim, Hyoung Ryeol Choi and Seunghyun Baik, "Highly conductive, printable and stretchable composite films of carbon nanotubes and silver" Nature Nanotechnology, 5, 853 (2010)

SUMMARY OF THE INVENTION

Problems to be Solved by the Invention

When a circuit is formed using a stretchable conductive paste, a wiring width of 5 mm or less is generally required from the viewpoint of device miniaturization. However, as the wiring width becomes narrower, the stress applied to the wiring line when the base material is elongated increases, so that the resistance increase when the base material is elongated many times becomes significant. The conductive paste composition that has already been disclosed has a problem that the clothes-type wearable device has poor washing durability because disconnection occurs only after the base material is elongated several times. The present invention has been made paying attention to the above-described circumstances, and it is an object of the present invention to provide a stretchable conductive paste capable of forming a wiring line having a small resistance increase upon repeated stretching.

The stretchable conductor composition is mainly composed of conductive particles and a flexible resin. As such a stretchable conductor, a composition in which an elastomer such as rubber is used as a resin binder and carbon black or metal particles are blended is generally known. Such a stretchable conductor composition is formed through a paste or slurry obtained by mixing, dissolving, and dispersing a solvent or the like as necessary to the conductive particles and the precursor of the crosslinked elastomer. When the paste is used, it becomes easy to form a wiring pattern by screen printing or the like. However, using only such an elastomer as the resin binder, disconnection occurs only by elongating the base material several times.

In addition, the paste is printed on the base material and then undergoes a drying and curing step. However, in a type that imparts repeated stretch resistance by crosslinking the binder, a relatively high processing temperature is required to promote the crosslinking reaction. On the other hand, as a base material of such a flexible material, naturally, a flexible material is preferable. However, since such a material generally has low heat resistance, in the case of materials of a type of forming such a crosslinked structure by a curing process, the selection range of the base is narrowed.

On the other hand, when no crosslinking agent is added to the conductive paste, there is no need to raise the temperature to the crosslinking reaction temperature and the material selection range of a printing device is widened. However, the coating film is not crosslinked so that the coating strength is insufficient. Therefore, the resistance increase during repeated elongation becomes significant.

Solutions to the Problems

As a result of intensive studies to achieve the above object, the present inventors have found a composition that can expand and contract several thousand times even if the line width is narrow by blending a urethane elastomer having a specific urethane group amount as a resin binder into a paste component, to thereby arrive at the following invention.

That is, the present invention has the following configurations.

[1] A stretchable conductor forming paste comprising at least:
a conductive filler;
a polyurethane elastomer; and
an organic solvent, wherein
a Tg of the polyurethane elastomer is −60° C. to −10° C., and
a urethane group concentration calculated by the following formula is 3000 to 4500 m equivalent/kg:

Urethane group concentration (m equivalent/kg)=(W/(X/Y))/Z×10$^6$ where W represents a mass of isocyanate constituting a polyurethane resin,
X represents a molecular weight of isocyanate,
Y represents an isocyanate number per molecule of isocyanate, and
Z represents a total mass of raw materials constituting the polyurethane resin.

[2] The stretchable conductor forming paste according to the above [1], wherein the conductive filler is silver particles.

[3] The stretchable conductor forming paste according to the above [1] or [2], wherein, when a total amount of components excluding the solvent is 100 parts by mass, a total of the conductive filler is 70 to 95 parts by mass, and an amount of the polyurethane elastomer is 5 to 30 parts by mass.

[4] The stretchable conductor forming paste according to any one of the above [1] to [3], comprising at least one carbon material selected from carbon black and graphite as the conductive filler.

[5] A stretchable conductor comprising at least:
a conductive filler; and
a polyurethane elastomer, wherein
a Tg of the polyurethane elastomer is −60° C. to −10° C., and
a urethane group concentration calculated by the following formula is 3000 to 4500 m equivalent/kg:

Urethane group concentration (m equivalent/kg)=(W/(X/Y))/Z×10$^6$ where W represents a mass of isocyanate constituting a polyurethane resin,
X represents a molecular weight of isocyanate,
Y represents an isocyanate number per molecule of isocyanate, and
Z represents a total mass of raw materials constituting the polyurethane resin.

[6] The stretchable conductor according to the above [5], wherein the conductive filler is silver particles.

[7] The stretchable conductor according to the above [5] or [6], wherein, when a total amount of components excluding a solvent is 100 parts by mass, a total of the conductive filler is 70 to 95 parts by mass, and an amount of the polyurethane elastomer is 5 to 30 parts by mass.

[8] The stretchable conductor according to any one of the above [5] to [7], comprising at least one carbon material selected from carbon black and graphite as the conductive filler.

[9] A stretchable electronic component comprising an electrical wiring line made of the stretchable electric conductor according to any one of the above [5] to [8].

[10] A clothes-type electronic device comprising an electrical wiring line made of the stretchable electric conductor according to any one of the above [5] to [8].

Effect of the Invention

A wiring line manufactured by printing a conductive paste using a urethane elastomer having a urethane group equivalent of 3000 or less per 1000 kg of resin as a binder has a weak interaction between silver and the urethane group contained in the paste, and it is repeatedly tested several hundred times to impair conductivity. Therefore, it is not suitable for wearable applications that are supposed to be used repeatedly several thousand times. When the urethane elastomer having a urethane group amount of 3000 or less per 1000 kg of resin is cross-linked, the interaction between the resin and silver will improve and it will be possible to use the wiring line repeatedly. In general, drying at a high temperature is required when the resin is cross-linked, but a stretchable base material generally has no heat resistance, and it is difficult to use a crosslinking agent. When the urethane group equivalent per 1000 kg of resin is 4500 or more, the interaction between the resin and silver becomes stronger, the dispersibility of the conductive particles is reduced, and the structure of the manufactured wiring line becomes non-uniform, so that the conductivity during repeated tests gets worse.

In the present invention, for the sake of convenience, the urethane group equivalent per 1000 kg of resin is expressed in m equivalent/kg. Here, m of m equivalent is milli representing 1/1000.

In the present invention, since the urethane elastomer having a urethane group equivalent within a specific range is used as the binder, the above problem can be avoided.

Since good printability can be maintained by keeping the urethane group equivalent within this range, a printed matter with fine lines can be formed. In addition, since the interaction between silver and the binder is high, high repeated stretchability can be maintained without using a crosslinking agent, so that a stretchable base material can be used and the selectivity of the base material can be increased. As a result, by using the conductive paste of the present invention, it is possible to print a line width of 5 mm or less, preferably 3 mm or less, and it is possible to print a pattern having a line interval of 1 mm or less.

MODE FOR CARRYING OUT THE INVENTION

Metal-based conductive particles of the present invention are particles made of a metal-based material having a specific resistance of $1\times10^{-2}$ Ωcm or less and having a particle size of 0.5 μm or more and 5 μm or less. Examples of the material having a specific resistance of $1\times10^{-2}$ Ωcm or less include metals, alloys, and doped semiconductors. As the conductive particles preferably used in the present invention, there can be used metals such as silver, gold, platinum, palladium, copper, nickel, aluminum, zinc, lead, and tin, alloy particles such as brass, bronze, white copper, and solder, hybrid particles such as silver-coated copper, metal-plated polymer particles, metal-plated glass particles, metal-coated ceramic particles, and the like.

In the present invention, it is preferable to mainly use flaky silver particles or amorphous aggregated silver powder. Here, "mainly use" here means to use it as the conductive particles at 90% by mass or more. The amorphous aggregated powder is a three-dimensional aggregate of spherical or irregular primary particles. The amorphous aggregated powder and flaky powder are preferable because they have a specific surface area larger than that of spherical powder and the like and can form a conductive network even with a low filling amount. Since the amorphous aggregated powder is not in a monodispersed form, the particles are in physical contact with each other, so that it is easy to form a conductive network. Therefore, the amorphous aggregated powder is further preferable.

Regarding the particle size of the conductive particles, the average particle size (50% D) measured by the dynamic light scattering method is 0.5 to 6 μm, more preferably 0.7 to 5.0 μm. When the average particle size exceeds a predetermined range, it becomes difficult to form a fine wiring line, and clogging occurs in the case of screen printing. When the average particle size is less than 0.5 μm, it is impossible to make contact between particles at low filling, and conductivity may deteriorate.

In the present invention, it is preferable to use carbon black having a DBP oil absorption of 100 to 550. There are many types of carbon black that differ in raw materials and production methods, each having its own characteristics. The DBP oil absorption is a parameter indicating the liquid absorption and retention performance of carbon black, and is measured based on ISO4656: 2012. In the present invention, the DBP oil absorption is preferably 160 or more and 530 or less, more preferably 210 or more and 510 or less, still more preferably 260 or more and 500 or less. When the DBP oil absorption is less than this range, the spaces between the lines are likely to be filled when fine lines are printed, and the fine line printability deteriorates. Further, when the DBP oil absorption exceeds this range, the viscosity of the paste tends to increase, and it is necessary to increase the blending amount of the solvent for viscosity adjustment. Thus, the solvent tends to bleed between the lines when lines are printed, and similarly, the fine line printability is reduced.

The blending amount of carbon black is 0.5% by mass or more and 2.0% by mass or less, preferably 0.7% by mass or more and 1.6% by mass or less, based on the total amount of the metal-based filler and carbon black.

In the present invention, non-conductive particles having an average particle size of 0.2 μm or more and 10 μm or less may be included. The non-conductive particles in the present invention are mainly metal oxide particles, and there can be used silicon oxide, titanium oxide, magnesium oxide, calcium oxide, aluminum oxide, iron oxide, metal sulfate, metal carbonate, metal titanate, and the like. In the present invention, it is preferable to use barium sulfate particles among such non-conductive particles.

As the elastomer (flexible resin) in the present invention, there can be used a urethane elastomer preferably having an elastic modulus of 1 to 1000 MPa and preferably having a glass transition temperature in the range of −60° C. to −10° C.

The elastic modulus of the elastomer is preferably 3 to 600 MPa, more preferably 10 to 500 MPa, still more preferably 15 to 300 MPa, still further more preferably 20 to 200 MPa, particularly preferably 25 to 150 MPa.

The urethane resin of the present invention can be obtained by reacting a soft segment made of a polyether-based, polyester-based, or polycarbonate-based polyol with a hard segment made of diisocyanate or the like. As the soft segment component, polyester polyol is more preferable because of the degree of freedom in molecular design.

Examples of the polyether polyol in the present invention include polyethylene glycol, polypropylene glycol, polypropylene triol, polypropylene tetraol, polytetramethylene glycol, polytetramethylene triol, polyalkylene glycol such as a copolymer obtained by copolymerizing a monomer material such as cyclic ether for synthesizing these, derivatives obtained by introducing side chains or branched structures to these, modified products, mixtures thereof, and the like. Of these, polytetramethylene glycol is preferred. The reason is that the mechanical properties are excellent.

As the polyester polyol in the present invention, there can be used aromatic-based polyester polyol, aromatic/aliphatic copolymer polyester polyol, aliphatic polyester polyol, and alicyclic polyester polyol. As the polyester polyol in the present invention, either a saturated type or an unsaturated type may be used. Of these, aliphatic polyester polyol is preferred.

Commercially available products can also be used as the aliphatic polyester polyol. Specific examples of the commercially available products include, for example, Polylite ODX-688, ODX-2044, ODX-240, and ODX-2376 (manufactured by DIC Corporation), Kuraray polyol P-2010, P-2050, and P-1010 (Kuraray), Teslack 2461, 2455, and 2469 (manufactured by Hitachi Chemical Company), and the like.

Examples of the polycaprolactone diol in the present invention include polycaprolactone diol compounds obtained by ring-opening addition reaction of lactones such as γ-butyllactone, ε-caprolactone, and δ-valerolactone.

Examples of commercially available products of polycarbonate diol compounds that can be used in the present invention include Kuraray Polyol C series manufactured by Kuraray Co., Ltd., Duranol series manufactured by Asahi Kasei Chemicals Corporation, and the like. Examples include Kuraray polyol C-1015N, Kuraray polyol C-1065N, Kuraray polyol C-2015N, Kuraray polyol C2065N, Kuraray polyol C-1050, Kuraray polyol C-1090, Kuraray polyol C-2050, Kuraray polyol C-2090, DURANOL-T5650E, DURANOL-T5651, and DURANOL-T5652.

Examples of the diisocyanate compound in the present invention include aromatic diisocyanates such as 2,4-tolylene diisocyanate, 2,6-tolylene diisocyanate, p-phenylene diisocyanate, 4,4'-diphenylmethane diisocyanate, m-phenylene diisocyanate, 3,3'-dimethoxy-4, 4'-biphenylene diisocyanate, 2,6-naphthalene diisocyanate, 3,3'-dimethyl-4,4'-biphenylene diisocyanate, 4,4'-diphenylene diisocyanate, 4,4'-diisocyanate diphenyl ether, 1,5-naphthalene diisocyanate, and m-xylene diisocyanate, aliphatics of 1,6-hexane diisocyanate, isophorone diisocyanate, 4,4'-diphenylmethane diisocyanate, and hydrogenated xylylene diisocyanate (ortho, meta, para), and alicyclic diisocyanate. Among these, 4,4'-diphenylmethane diisocyanate, 2,4-tolylene diisocyanate, 2,6-tolylene diisocyanate, and isophorone diisocyanate are preferable. Moreover, as necessary, the isocyanate may be used together, and a tri- or more functional polyisocyanate compound may be used together.

As necessary, the polyurethane resin of the present invention may be copolymerized with a diol compound or the like generally called a chain extender.

Examples of the diol compound used as a chain extender include aliphatic glycols such as ethylene glycol, diethylene glycol, triethylene glycol, propylene glycol, dipropylene glycol, tripropylene glycol, 1,3-propanediol, 2-methyl-1,3-propanediol, 2-methyl-2-propyl-1,3-propanediol, 2-butyl-2-ethyl-1,3-propanediol, 2-butyl-2-hexyl-1,3-propanediol, 1,2-butanediol, 1,3-butanediol, 1,4-butanediol, 2,3-butanediol, 1,5-pentanediol, 2-methyl-2,4-pentanediol, 3-methyl-1,5-pentanediol, 2,2,4-trimethyl-1,3-pentanediol, neopentyl glycol, 1,6-hexanediol, 2-ethyl-1,3-hexanediol, 2,5-dimethyl-2,5-hexanediol, 1,8-octanediol, 2-methyl-1,8-octanediol, and 1,9-nonanediol. Alternatively, low molecular weight triols such as trimethylolpropane and triethanolamine, diamine compounds such as diethylamine and 4,4'-diaminodiphenylmethane, and trimethylolpropane can be given. Among these, 1,6-hexanediol is particularly preferable.

The glass transition temperature of the polyurethane resin of the present invention is preferably 0° C. or less, more preferably −60° C. or more and −10° C. or less, most preferably −50° C. or more and −20° C. or less. When the glass transition temperature exceeds 0° C., the elongation of the manufactured conductive coating film becomes small, and the resistance increase at the time of elongation may be deteriorated. Moreover, when it is less than −60° C., the manufactured conductive coating film may produce blocking. The reduced viscosity is 0.2 dl/g or more and 3.0 dl/g or less, preferably 0.3 dl/g or more and 2.5 dl/g or less, more preferably 0.4 dl/g or more and 2.0 dl/g or less. When it is less than 0.2 dl/g, the conductive coating film becomes brittle and the resistance increase at the time of elongation may be worsen. Moreover, when it exceeds 3.0 dl/g, the solution viscosity of a polyurethane resin composition may become high and handling may become difficult.

When a polyurethane resin is produced, stannous octylate, dibutyltin dilaurate, triethylamine, bismuth metal, or the like may be used as a catalyst.

In the stretchable conductor forming paste of the present invention, when the total amount of components excluding the solvent is 100 parts by mass, the total amount of the metal conductive filler and carbon black is 70 to 95 parts by mass, and the amount of the urethane elastomer is 5 to 30 parts by mass. Preferably, the total of the metal conductive filler and carbon black is 75 to 90 parts by mass, and the amount of the urethane elastomer is 10 to 25 parts by mass.

The paste for forming a stretchable conductor of the present invention contains a solvent. The solvent used in the present invention is an organic solvent having a boiling point of 200° C. or more and a saturated vapor pressure at 20° C. of 20 Pa or less. When the boiling point of the organic solvent is too low, the solvent volatilizes during the paste production process or use of the paste, and there is a concern that the component ratio of the conductive paste is likely to change. On the other hand, when the boiling point of the organic solvent is too high, the amount of residual solvent in the dry cured coating film increases, and there is a concern that the reliability of the coating film is reduced. In addition, since the drying and curing take a long time, the edge sagging during the drying process increases and it becomes difficult to keep the space between the wiring lines narrow.

As the organic solvent in the present invention, there can be used benzyl alcohol (vapor pressure: 3 Pa, boiling point: 205° C.), tarpionele (vapor pressure: 3.1 Pa, boiling point: 219° C.), diethylene glycol (vapor pressure: 0.11 Pa, boiling point: 245° C.), diethylene glycol monoethyl ether acetate (vapor pressure: 5.6 Pa, boiling point 217° C.), diethylene glycol monobutyl ether acetate (vapor pressure: 5.3 Pa, boiling point: 247° C.), diethylene glycol dibutyl ether (vapor pressure: 0.01 mmHg or less, boiling point: 255° C.), triethylene glycol (vapor pressure: 0.11 Pa, boiling point: 276° C.), triethylene glycol monomethyl ether (vapor pressure: 0.1 Pa or less, boiling point: 249° C.), triethylene glycol monoethyl ether (vapor pressure: 0.3 Pa, boiling point: 256° C.), triethylene glycol monobutyl ether (vapor pressure: 1 Pa, boiling point: 271° C.), tetraethylene glycol (vapor pressure: 1 Pa, boiling point: 327° C.), tetraethylene glycol monobutyl ether (vapor pressure: 0.01 Pa or less, boiling point: 304° C.), tripropylene glycol (vapor pressure: 0.01 Pa or less, boiling point: 267° C.), tripropylene glycol monomethyl ether (vapor pressure: 3 Pa, boiling point: 243° C.), and diethylene glycol monobutyl ether (vapor pressure: 3 Pa, boiling point: 230° C.).

The solvent in the present invention may contain two or more of them as necessary. Such an organic solvent is appropriately contained so that the paste for forming the stretchable conductor composition has a viscosity suitable for printing or the like.

The blending amount of the organic solvent in the present invention is 5 to 40 parts by mass, preferably 10 to 30 parts by mass, when the total mass of the conductive particles, non-conductive particles, and non-crosslinked elastomer is 100 parts by mass.

The stretchable conductor forming paste of the present invention can be obtained by mixing and dispersing conductive particles being a material, and non-conductive particles, an urethane elastomer, and a solvent which are preferably blended, using a dispersing machine such as a dissolver, a three-roll mill, a self-revolving mixer, an attritor, a ball mill, or a sand mill.

The stretchable conductor forming paste of the present invention can be imparted with printability, adjusted in color tone, and blended with known organic and inorganic additives such as, leveling, antioxidants, ultraviolet absorbers, and the like without impairing the contents of the present invention.

In the present invention, an electrical wiring line made of the stretchable conductor composition can be formed by directly printing an electrical wiring pattern on a fabric using the above-described stretchable conductor forming paste. As a printing method, there can be used a screen printing method, a planographic offset printing method, a paste jet method, a flexographic printing method, a gravure printing method, a gravure offset printing method, a stamping method, a stencil method, and the like. It is preferable to use the screen printing method or the stencil method in the present invention. A method of directly drawing a wiring line using a dispenser or the like may be interpreted as printing in a broad sense.

In the present invention, using the stretchable conductor paste thus obtained, preferably, an electrical wiring line having a line width of less than 3 mm and a line interval of 500 pm or less is formed by a printing method, and then, under atmospheric pressure, the electrical wiring line is dried at a temperature in the range of 75° C. to 120° C. In this manner, a stretchable electrical wiring line can be obtained.

The base material used for printing is a stretchable base material or a highly flexible material. The stretchable conductor forming paste of the present invention is used suitably for forming a stretchable electrical wiring line on a flexible sheet such as rubber or urethane, or on a fabric such as a woven fabric, a knitted fabric, a non-woven fabric, or a synthetic leather, which is an original fabric of clothes or textile products. In addition, the stretchable conductor forming paste can be printed after a flexible resin material such as polyurethane resin or rubber is entirely or partially applied on a fabric as a base in advance. Alternatively, the fabric may be temporarily hardened with a water-soluble resin to facilitate handling for printing. Further, it may be temporarily fixed to a harder plate material for printing.

The stretchable electrical wiring line composed of the stretchable conductor composition in the present invention maintains electrical conductivity even after 20% expanding and contracting is repeated 100 times, preferably maintains electrical conductivity even after 20% expanding and contracting is repeated 500 times, more preferably maintains electrical conductivity even after 20% expanding and contracting is repeated 1000 times.

In the present invention, the line width when the electrical wiring line is not stretched is less than 3 mm, more preferably 1 mm or less.

In the present invention, the width between the lines when the electrical wiring line is not stretched is 50 μm or more and 1 mm or less, more preferably 80 μm or more and 750 μm or less. When the line interval exceeds this range, not only the mounting density of the electronic circuit is lowered, but also the unevenness of the wiring surface becomes noticeable tactilely, and the feeling of strangeness increases when the electronic device is worn as clothes. On the other hand, if it is attempted to form a line interval less than this range, the printing plate is washed more frequently, the yield is lowered, and productivity is hindered.

The width/thickness ratio (aspect ratio) of the electrical wiring line of the present invention is in the range of 5 to 200, preferably 7 to 150, more preferably 10 to 100. When the aspect ratio exceeds this range, the cross-sectional area of the wiring line becomes small, and it becomes difficult to secure a necessary current capacity. On the other hand, in order to form a wiring line with an aspect ratio smaller than this range, a method with low material efficiency such as a lift-off method has to be adopted, and productivity is lowered.

The thickness of the stretchable conductor formed from the stretchable conductor paste in the present invention is preferably 2 to 60 μm, more preferably 3 to 40 μm, still more preferably 5 to 25 μm.

EXAMPLES

Hereinafter, the present invention will be described in more detail and specifically with reference to examples. The evaluation results in the examples were measured by the following methods.

<Sample Manufacture Method for Measuring Reduced Viscosity, Glass Transition Temperature, and Mechanical Properties>

A polyurethane resin composition was coated on a polypropylene film (pylen OT; 50 μm thickness) manufactured by Toyobo Co., Ltd. using an applicator having a gap of 300 μm and a width of 130 mm (the coated surface was 130 mm×200 mm). The coated material was fixed on cardboard, dried using a hot air dryer (DH42 manufactured by Yamato Scientific Co., Ltd.) at 120° C. for 30 minutes, and then cooled. Then, it was peeled from the polypropylene film and obtained the sample for evaluation.

<Reduced Viscosity>

0.1g of the sample prepared based on the above reduced viscosity sample preparation method was precisely weighed and placed in a volumetric flask of 25 ml. About 20 ml of phenol/tetrachloroethane=6/4 (mass ratio) mixed solvent was added and heated to dissolve the resin. After complete dissolution, phenol/tetrachloroethane=6/4 (mass ratio) mixed solvent was added up to 25 ml line at 30° C. The mixture was uniformly mixed and measured at 30° C. using a Ubbelohde viscosity tube.

<Glass Transition Temperature (Tg)>

5 mg of a sample resin was placed in an aluminum sample pan and was sealed, and was measured using a differential scanning calorimeter (DSC) DSC-7020 manufactured by Seiko Instruments Inc., up to 100° C. at a rate of temperature increase of 20° C./min, and the temperature at the intersection with the extended line of the base line of the glass transition temperature or less and the tangent indicating the maximum inclination in the transition portion was obtained.

<Mechanical Properties>

A piece with a sample size of 10 mm×50 mm was cut out from the sample prepared based on the sample preparation method for measuring mechanical properties, clamped by 20 mm from upper and lower sides each on the sample fixing chuck of a tensile tester (RTA-100 manufactured by ORIENTEC CORPORATION), and measured under the conditions of an inter-chuck distance of 10 mm, a tensile speed of 20 mm/min, and a temperature of 25° C. and 60 RH %, and the elastic modulus and elongations were measured five times from the S-S curve and averaged.

<Urethane Group Concentration>

A urethane group concentration is calculated by the following formula.

Urethane group concentration (m equivalent/kg)=$(W/(X/Y))/Z \times 10^6$ where W represents a mass of isocyanate constituting a polyurethane resin, X represents a molecular weight of isocyanate, Y represents an isocyanate number per molecule of isocyanate, and Z represents a total mass of raw materials constituting the polyurethane resin.

<Manufacture of Sample for Repeated Stretching Measurement>

A conductive paste was applied on a stretchable urethane sheet with a thickness of 100 μm using a screen printer and dried at 120° C. for 30 minutes to manufacture a printed matter having a conductive film with a line width of 1 mm and a film thickness of about 20 μm.

<Evaluation of Initial Resistance Value and Resistance Value During Stretching>

The initial resistance value was calculated by measuring the resistance of a wiring object in a natural state (elongation rate 0%). The resistance value was measured using a PC720M manufactured by SANWA. The resistance value during stretching was calculated in the same manner.

<Evaluation of Repeated Stretchability>

Using a repeated durability tester (TIQ-100 manufactured by RHESCA CO., LTD), the sample film was repeatedly subjected to repeated stretching at the elongation rate of 20% of repeatedly changing its state between a state where the sample film is elongated by 20% of its original length and a state where the sample film is returned to its original length, and the number of times until the conduction was stopped (limit number) was measured. The elongation speed and the speed for returning to the original length were both 10 mm/second.

<Resin Production Example 1>
Synthesis of Polyurethane Resin Composition (A)

In a four-necked flask of 1 L, 100 parts of ODX-2044 (polyester diol manufactured by DIC) was placed, and 30 parts of 1,6-hexanediol (manufactured by Ube Industries, Ltd.) as a chain extender was placed in 98 parts of diethylene glycol monoethyl ether acetate, and these were set in a mantle heater. A stir bar with a stirring seal, a reflux condenser, a temperature detector, and a ball plug were set in the flask and dissolved by stirring at 50° C. for 30 minutes. 53 parts of T-100 (isocyanate produced by Tosoh Corporation) and 0.1 part of clibutyltin dilaurate as a catalyst were added. When the temperature rise due to the reaction heat settled, the temperature was raised to 90° C. and reacted for 4 hours to obtain a polyurethane resin composition (A). The properties of the obtained resin are shown in Table 1.

<Resin Production Example 2>
Synthesis of Polyurethane Resin Composition (B)

In a four-necked flask of 1 L, 100 parts of ODX-2044 (polyester diol manufactured by DIC) was placed, and 33 parts of 1,6-hexanediol (manufactured by Ube Industries, Ltd.) as a chain extender was placed in 103 parts of diethylene glycol monoethyl ether acetate, and these were set in a mantle heater. A stir bar with a stirring seal, a reflux condenser, a temperature detector, and a ball plug were set in the flask and dissolved by stirring at 50° C. for 30 minutes. 58 parts of T-100 (isocyanate produced by Tosoh Corporation) and 0.1 part of dibutyltin dilaurate as a catalyst were added. When the temperature rise due to the reaction heat settled, the temperature was raised to 90° C. and reacted for 4 hours to obtain a polyurethane resin composition (B). The properties of the obtained resin are shown in Table 1.

<Resin Production Example 3>
Synthesis of Polyurethane Resin Composition (C)

In a four-necked flask of 1 L, 100 parts of ODX-2044 (polyester diol manufactured by DIC) was placed, and 24 parts of 1,6-hexanediol (manufactured by Ube Industries, Ltd.) as a chain extender was placed in 91 parts of diethylene glycol monoethyl ether acetate, and these were set in a mantle heater. A stir bar with a stirring seal, a reflux condenser, a temperature detector, and a ball plug were set in the flask and dissolved by stirring at 50° C. for 30 minutes. 45 parts of T-100 (isocyanate produced by Tosoh Corporation) and 0.1 part of dibutyltin dilaurate as a catalyst were added. When the temperature rise due to the reaction heat settled, the temperature was raised to 90° C. and reacted for 4 hours to obtain a polyurethane resin composition (C). The properties of the obtained resin are shown in Table 1.

<Resin Production Example 4>
Synthesis of Polyurethane Resin Composition (D)

In a four-necked flask of 1 L, 100 parts of ODX-2044 (polyester diol manufactured by DIC) was placed, and 40 parts of 1,6-hexanediol (manufactured by Ube Industries, Ltd.) as a chain extender was placed in 112 parts of diethylene glycol monoethyl ether acetate, and these were set in a mantle heater. A stir bar with a stirring seal, a reflux condenser, a temperature detector, and a ball plug were set in the flask and dissolved by stirring at 50° C. for 30 minutes. 68 parts of T-100 (isocyanate produced by Tosoh Corporation) and 0.1 part of clibutyltin dilaurate as a catalyst were added. When the temperature rise due to the reaction heat settled, the temperature was raised to 90° C. and reacted for 4 hours to obtain a polyurethane resin composition (D). The properties of the obtained resin are shown in Table 1.

<Resin Production Example 5>
Synthesis of Polyurethane Resin Composition (E)

In a four-necked flask of 1L, 100 parts of ODX-2044 (polyester diol manufactured by DIC) was placed, and 20 parts of 1,6-hexanediol (manufactured by Ube Industries, Ltd.) as a chain extender was placed in 85 parts of diethylene glycol monoethyl ether acetate, and these were set in a mantle heater. A stir bar with a stirring seal, a reflux condenser, a temperature detector, and a ball plug were set in the flask and dissolved by stirring at 50° C. for 30 minutes. 38 parts of T-100 (isocyanate produced by Tosoh Corporation) and 0.1 part of dibutyltin dilaurate as a catalyst were added. When the temperature rise due to the reaction heat settled, the temperature was raised to 90° C. and reacted for 4 hours to obtain a polyurethane resin composition (E). The properties of the obtained resin are shown in Table 1.

<Resin Production Example 6>
Synthesis of Polyurethane Resin Composition (E)

In a four-necked flask of 1 L, 100 parts of ODX-2044 (polyester diol manufactured by DIC) was placed, and 73 parts of 1,6-hexanediol (manufactured by Ube Industries, Ltd.) as a chain extender was placed in 160 parts of diethylene glycol monoethyl ether acetate, and these were set in a mantle heater. A stir bar with a stirring seal, a reflux condenser, a temperature detector, and a ball plug were set in the flask and dissolved by stirring at 50° C. for 30 minutes. 125 parts of T-100 (isocyanate produced by Tosoh Corporation) and 0.1 part of dibutyltin dilaurate as a catalyst were added. When the temperature rise due to the reaction heat settled, the temperature was raised to 90° C. and reacted for 4 hours to obtain a polyurethane resin composition (F). The properties of the obtained resin are shown in Table 1.

TABLE 1

|  | Reduced Viscosity (dl/g) | Glass transition temperature (° C.) | Urethane group concentration (m equivalent/kg) | Elastic modulus (MPa) | Elongation (%) |
|---|---|---|---|---|---|
| Composition A | 0.81 | −20 | 3325 | 70 | 1180 |
| Composition B | 0.83 | −15 | 3486 | 114 | 1050 |

TABLE 1-continued

|  | Reduced Viscosity (dl/g) | Glass transition temperature (° C.) | Urethane group concentration (m equivalent/kg) | Elastic modulus (MPa) | Elongation (%) |
|---|---|---|---|---|---|
| Composition C | 0.76 | −32 | 3057 | 52 | 1430 |
| Composition D | 0.9 | −10 | 3753 | 125 | 960 |
| Composition E | 0.65 | −42 | 2761 | 30 | 1440 |
| Composition F | 0.72 | 12 | 4816 | 156 | 780 |

<Manufacture and Evaluation of Conductive Paste>

First, the binder resin is dissolved in half the amount of the solvent specified, and the metal particles, the treating agent, and the remaining solvent were added to the resulting solution, and premixed. Next, the remaining solvent is dispersed in a three-roll mill to be turned into a paste, and conductive pastes of Examples 1 to 9 and Comparative Examples 1 to 5 shown in Tables 2 and 3 were obtained. The evaluation results of the obtained conductive paste are shown in Table 2 and Table 3.

In the table, the metal-based particles Ag01 are SPHO2J (conductive particles, silver powder, average particle size: 1 p.m) manufactured by Mitsui Mining & Smelting Co., Ltd.

The metal-based particles Ag02 are silver particles AgC-A (conductive particles, silver powder, average particle size of 3.5 μm) manufactured by Fukuda Metal Foil Powder Co., Ltd.

Carbon-based particle CB01 is Ketjen Black EC600JD (DBP oil absorption 495) manufactured by Lion Specialty Chemicals Co., Ltd.

Solvent: ECA is diethylene glycol monoethyl ether acetate.

Additive: Barium sulfate is B-34 (particle size of 0.3 μm) manufactured by Sakai Chemical Industry Co., Ltd.

Additive: Leveling agent is MK Conk manufactured by Kyoeisha Chemical Co., Ltd.

TABLE 2

|  |  |  |  | Example 1 | Example 2 | Example 3 | Example 4 | Example 5 | Example 6 | Example 7 | Example 8 |
|---|---|---|---|---|---|---|---|---|---|---|---|
| Paste composition ratio [parts by mass] | Binder resin | A |  | 6.8 | 9.3 | 13.3 | 19.8 | 12.1 | 10.5 | — | — |
|  |  | B |  | — | — | — | — | — | — | 9.4 | 10.5 |
|  |  | C |  | — | — | — | — | — | — | — | — |
|  |  | D |  | — | — | — | — | — | — | — | — |
|  |  | E |  | — | — | — | — | — | — | — | — |
|  |  | F |  | — | — | — | — | — | — | — | — |
|  | Metal-based particle | Ag01 |  | 73 | 70.1 | 66.5 | 59.6 | 67 | — | 70.4 | — |
|  |  | Ag02 |  | — | — | — | — | — | 69.3 | — | 69.3 |
|  | Carbon-based particle | CB01 |  | — | — | — | — | 0.7 | — | — | — |
|  | Solvent | ECA |  | 18.5 | 18.8 | 18.5 | 18.7 | 18.5 | 18.5 | 18.5 | 18.5 |
|  | Additive | Barium sulfate |  | 1.3 | 1.4 | 1.3 | 1.3 | 1.3 | 1.3 | 1.3 | 1.3 |
|  |  | Leveling agent |  | 0.4 | 0.4 | 0.4 | 0.4 | 0.4 | 0.4 | 0.4 | 0.4 |
| Property | Stretch resistance | Limit number |  | 2700 | 3000 | 2000 | 1200 | 2900 | 2500 | 4000 | 3500 |
|  | Initial specific resistance | Ω cm |  | $1.5 \times 10^{-4}$ | $2.0 \times 10^{-4}$ | $3.2 \times 10^{-4}$ | $4.5 \times 10^{-4}$ | $2.1 \times 10^{-4}$ | $2.4 \times 10^{-4}$ | $1.5 \times 10^{-4}$ | $2.2 \times 10^{-4}$ |
| Urethane group concentration |  | m equivalent/kg |  | 3300 | 3300 | 3300 | 3300 | 3300 | 3300 | 3465 | 3465 |

TABLE 3

|  |  |  | Example 9 | Example 10 | Example 11 | Comparative Example 1 | Comparative Example 2 | Comparative Example 3 | Comparative Example 4 |
|---|---|---|---|---|---|---|---|---|---|
| Paste composition ratio [parts by mass] | Binder resin | A | — | — | 6.3 | — | — | 27.3 | 3.5 |
|  |  | B | — | — | — | — | — | — | — |
|  |  | C | 9.4 | — | 6.3 | — | — | — | — |
|  |  | D | — | 10.4 | — | — | — | — | — |
|  |  | E | — | — | — | — | 8.7 | — | — |
|  |  | F | — | — | — | 10.4 | — | — | — |
|  | Metal-based particle | Ag01 | 70.4 | 69.4 | 67.2 | 69.4 | 71.1 | 52.5 | 76.3 |
|  |  | Ag02 | — | — | — | — | — | — | — |
|  | Carbon-based particle | CB01 | — | — | — | — | — | — | — |
|  | Solvent | ECA | 18.5 | 18.5 | 18.5 | 18.5 | 18.5 | 18.5 | 18.5 |
|  | Additive | Barium sulfate | 1.3 | 1.3 | 1.3 | 1.3 | 1.3 | 1.3 | 1.3 |
|  |  | Leveling agent | 0.4 | 0.4 | 0.4 | 0.4 | 0.4 | 0.4 | 0.4 |

TABLE 3-continued

|  |  |  | Example 9 | Example 10 | Example 11 | Comparative Example 1 | Comparative Example 2 | Comparative Example 3 | Comparative Example 4 |
|---|---|---|---|---|---|---|---|---|---|
| Property | Stretch resistance | Limit number | 2000 | 2500 | 3200 | 500.0 | 200.0 | 70.0 | not printed |
|  | Initial specific resistance | Ω cm | $2.7 \times 10^{-4}$ | $2.2 \times 10^{-4}$ | $2.0 \times 10^{-4}$ | $1.8 \times 10^{-4}$ | $4.5 \times 10^{-4}$ | $8.0 \times 10^{-4}$ | not printed |
| Urethane group concentration |  | m equivalent/kg | 3033 | 3736 | mixture | 4864 | 2700 | 3300 | 3300 |

INDUSTRIAL APPLICABILITY

As described above, the stretchable conductor forming paste according to the present invention is capable of printing fine lines, has stretchability, and further includes an electrical wiring line composed of stretchable conductors having a narrower wiring interval and wiring width. By this, it is excellent in the repeated bending property of the wiring part, repeated twisting property, and repeated stretchability, and also there is little discomfort at the time of wearing.

The method of the clothes-type electronic device according to the present invention can be applied to a wearable device that detects information held by a human body, that is, bioelectric potential such as myoelectric potential and cardiac potential, biological information such as body temperature, pulse, blood pressure, and the like by a sensor provided to clothes, clothes that incorporate an electrical heating device, a wearable device that incorporates a sensor for measuring clothes pressure, a wear that measures a body size using clothes pressure, a socks-shaped device for measuring pressure on the sole, clothes that integrate flexible solar cell modules in textiles, a wiring part of a tent, a bag, or the like, a wiring part of a low-frequency treatment device with a joint, a thermotherapy machine, or the like, and a sensing unit such as bending degree. Such a wearable device can be applied not only to the human body but also to animals such as pets and livestock, and mechanical devices having a stretching part, a bent part, or the like, and it can also be used as an electrical wiring line for systems that are used by connecting a mechanical device such as a robot artificial arm or a robot artificial foot and the human body. It is also useful as a wiring material for an implant device that is used by being embedded in the body.

The invention claimed is:

1. A stretchable conductor forming paste comprising at least:
   a conductive filler;
   a polyurethane elastomer; and
   an organic solvent, wherein
   a glass transition temperature (Tg) of the polyurethane elastomer is −60° C. to −10° C., and
   a urethane group concentration of the polyurethane elastomer calculated by the following formula is 3000 to 4500 m equivalent/kg:
   Urethane group concentration (m equivalent/kg)=(W/(X/Y))/Z×$10^6$
   where W represents a mass of isocyanate constituting a polyurethane resin,
   X represents a molecular weight of isocyanate,
   Y represents an isocyanate number per molecule of isocyanate, and
   Z represents a total mass of raw materials constituting the polyurethane resin,
   wherein, when a total amount of components excluding the solvent is 100 parts by mass, a total of the conductive filler is 70 to 95 parts by mass, and an amount of the polyurethane elastomer is 5 to 30 parts by mass.

2. The stretchable conductor forming paste according to claim 1, wherein the conductive filler is silver particles.

3. The stretchable conductor forming paste according to claim 1, wherein the conductive filler comprises at least one carbon material selected from the group consisting of carbon black and graphite.

4. A stretchable conductor comprising at least:
   a conductive filler; and
   a polyurethane elastomer, wherein
   a glass transition temperature (Tg) of the polyurethane elastomer is −60° C. to −10° C., and
   a urethane group concentration of the polyurethane elastomer calculated by the following formula is 3000 to 4500 m equivalent/kg:
   Urethane group concentration (m equivalent/kg)=(W/(X/Y))/Z×$10^6$
   where W represents a mass of isocyanate constituting a polyurethane resin,
   X represents a molecular weight of isocyanate,
   Y represents an isocyanate number per molecule of isocyanate, and
   Z represents a total mass of raw materials constituting the polyurethane resin,
   wherein, when a total amount of components excluding a solvent is 100 parts by mass, a total of the conductive filler is 70 to 95 parts by mass, and an amount of the polyurethane elastomer is 5 to 30 parts by mass.

5. The stretchable conductor according to claim 4, wherein the conductive filler is silver particles.

6. The stretchable conductor according to claim 4, wherein the conductive filler comprises at least one carbon material selected from the group consisting of carbon black and graphite.

7. A stretchable electronic component comprising an electrical wiring line made of the stretchable electric conductor according to claim 4.

8. A clothes-type electronic device comprising an electrical wiring line made of the stretchable electric conductor according to claim 4.

* * * * *